United States Patent [19]

Dillon et al.

[11] Patent Number: 5,730,751
[45] Date of Patent: Mar. 24, 1998

[54] SCALPEL

[75] Inventors: Jagmohanbir Singh Dillon, Bonython; William Leonard Mobbs, Wanniassa, both of Australia

[73] Assignee: Noble House Group Pty. Ltd., Australia

[21] Appl. No.: 704,580

[22] PCT Filed: Mar. 17, 1995

[86] PCT No.: PCT/AU95/00157

§ 371 Date: Sep. 17, 1996

§ 102(e) Date: Sep. 17, 1996

[87] PCT Pub. No.: WO95/24855

PCT Pub. Date: Sep. 21, 1995

[30] Foreign Application Priority Data

Mar. 17, 1994 [AU] Australia ............... PM4564

[51] Int. Cl.$^6$ ............... A61B 17/32
[52] U.S. Cl. ............... 606/167; 30/2; 30/151
[58] Field of Search ............... 606/166, 167; 30/2, 151, 162, 164, 167, 286, 335

[56] References Cited

U.S. PATENT DOCUMENTS

| | | |
|---|---|---|
| 3,906,626 | 9/1975 | Riuli . |
| 5,201,748 | 4/1993 | Newman et al. . |
| 5,275,606 | 1/1994 | Abidin et al. . |
| 5,330,493 | 7/1994 | Haining ............... 606/167 |
| 5,344,424 | 9/1994 | Roberts et al. . |
| 5,411,512 | 5/1995 | Abidin et al. . |
| 5,417,704 | 5/1995 | Wonderly . |
| 5,481,804 | 1/1996 | Platts ............... 606/167 |
| 5,571,127 | 11/1996 | DeCampli ............... 606/167 |
| 5,571,128 | 11/1996 | Shapiro ............... 606/167 |
| 5,599,351 | 2/1997 | Haber et al. ............... 606/167 |

FOREIGN PATENT DOCUMENTS

| | | |
|---|---|---|
| 31999/93 | 7/1993 | Australia . |
| 57897/94 | 7/1994 | Australia . |

Primary Examiner—Michael Buiz
Assistant Examiner—William W. Lewis
Attorney, Agent, or Firm—Michael D. Bednarek; Kilpatrick Stockton LLP

[57] ABSTRACT

A scalpel that has a blade member; a handle adapted to receive a mandrel therein and having an opening; and a mandrel closely received within the handle. The mandrel can support the blade member and includes engagement structure for operative engagement by a user for movement of the mandrel within the handle. Biasing structure is provided for biasing the mandrel from an operative location adjacent the opening to an inoperative location within the handle, and restraining structure is provided for restraining the mandrel in the operative position against the action of the biasing means.

8 Claims, 4 Drawing Sheets

SCALPEL

TECHNICAL FIELD

This invention relates to a scalpel. As used herein, the term "scalpel" is used to denote a cutter, including cutters intended for use a surgical environment.

BACKGROUND ART

The emergence of HIV and other patient-to-patient transmissable diseases has encouraged the development of scalpels having some means for protecting the blade of the scalpel when the scalpel is not in use, or has performed its single use.

It is known to provide a scalpel with a guard or sheath which can be slid forward relative to the blade to shield the blade. Examples of such constructions are taught in International Patent Application WO 93/11916, European Patent Application 279 957, U.S. Pat. No. 5,275,606, U.S. Pat. No. 5,411,512, U.S. Pat. No. 3,906,626, U.S. Pat. No. 5,417,704, and Australian Patent Application 31999/93.

It is also known to have a retractable blade as, for example, shown in U.S. Pat. No. 5,201,748, U.S. Pat. 4,805,304 and U.S. Pat. No. 5,344,424.

The present invention relates to a scalpel having a retractable blade.

A problem associated with scalpels having blades which retract inside a handle is the likelihood that, depending on tolerances, the mandrel and hence blade can move laterally and/or vertically relative to the handle during a cutting operation. It will be understood that this is highly undesirable.

This problem is not associated with scalpels having guard or sheath because, in that case, the handle is integral with the blade.

DISCLOSURE OF INVENTION

This invention in one aspect resides in a scalpel including:
a handle;
a mandrel closely received within said handle, said mandrel being adapted to support a blade member and having engagement means for operative engagement by a user for movement of said mandrel within said handle;
biasing means for biasing said mandrel from an operative position to an inoperative position within said handle; and
restraining means for restraining said mandrel in said operative position against the action of said biasing means,
wherein said mandrel includes resilient means which bears against an inner surface of said handle when said mandrel is in said operative position.

Preferably, the resilient means are a pair of laterally and rearwardly extending wings.

The blade member may be supported on the mandrel in a number of ways. Thus the blade can be manufactured with lugs adapted to be received within apertures on the mandrel, or alternatively the blade may be supported and fixed on the mandrel by ultrasonic welding of a plastic mandrel about the blade shank. The blade can also be supported on the mandrel by rivets or other similar fastening means. However it is preferred that the mandrel includes mounting means for mounting the blade member thereon, the mounting means constituting mandrel stiffening means and being adapted to guide the mandrel for movement within the handle.

In a preferred single-use embodiment the scalpel may include locking means actuable upon retraction of the mandrel from the operative position to non-releasably lock the mandrel in the inoperative position.

The handle may be made from a range of suitable materials which may be quite rigid and not requiring stiffening. However it is preferred that the handle includes handle stiffening means.

In one preferred embodiment the opposite sides of the handle extend to form jaws and the handle stiffening means extend along the inside surfaces of the jaws. In such an arrangement the mounting means and the handle stiffening means may cooperate to guide the mandrel for movement in the handle.

It is preferred that the handle includes a longitudinally extending slot, the engagement means being adapted to extend through the slot. Preferably, the longitudinally extending slot is located on the upper surface of the handle although for varying ergonomic requirements in the implementation of special surgical techniques it may be desirable that the slot and the engagement means are located on each side surface or on the base of the handle.

The restraining means may include a projecting member on the engagement means and receiving means on the handle for releasably receiving the projecting member therein. The projecting member may be biased into engagement with the receiving means.

The locking means may be any suitable arrangement for ensuring that the blade, once retracted within the handle after use, cannot be re-used.

The biasing means may be any suitable means such as, for example, a compression spring. It is preferred that the biasing means is a tension spring attached to the mandrel and the end of the handle. Alternatively, resilient plastics, rubber or the like may be used to provide the biasing effect.

The blades and the handles are preferably colour coded for ease of recognition during surgical procedures.

It is preferred that the locking means is primed upon initial movement of the mandrel to the operative position. Thus, the blade member would be in the inoperative position prior to use, would be moved to the operative position for use, and may be locked in the inoperative position after use. That is, the scalpel would be a single use implement but would be packaged and transported in the inoperative configuration for safety. Preferably, the locking means includes a detent on one of the mandrel or the handle, stop means on the other of the mandrel or the handle, and detent actually means actuable upon movement of the mandrel to the operative position to bias the detent for locking engagement with the stop means when the mandrel is moved from the operative position to the inoperative position.

According to another broad aspect of the invention there is provided a mandrel for a scalpel, the mandrel being adapted to slide within a handle and comprising:
mounting means for mounting a blade member;
engagement means for operative engagement by a user; and
resilient means for resiliently engaging an inner surface of the handle.

The resilient means may take any form and may extend in any direction. However, it is preferred that the resilient means are laterally and rearwardly extending wings.

Preferably also, the mandrel includes restraining means in the form of a projecting member adapted to be received in receiving means disposed in the handle.

In a preferred embodiment manual force on the engagement means disengages the projecting member from receiving means to allow displacement of the mandrel relative to the handle. In one embodiment the mandrel is resilient and bifurcated whereby the manual force on the engagement means disengages the projecting member from the receiving means. Thereafter, the biasing means is operative to urge the mandrel to the inoperative position.

BRIEF DESCRIPTION OF DRAWINGS

In order that this invention may be more easily understood and put into practical effect, reference will now be made to the accompanying drawings which illustrate a preferred embodiment of the invention, wherein.

BEST MODE

Figure 1:
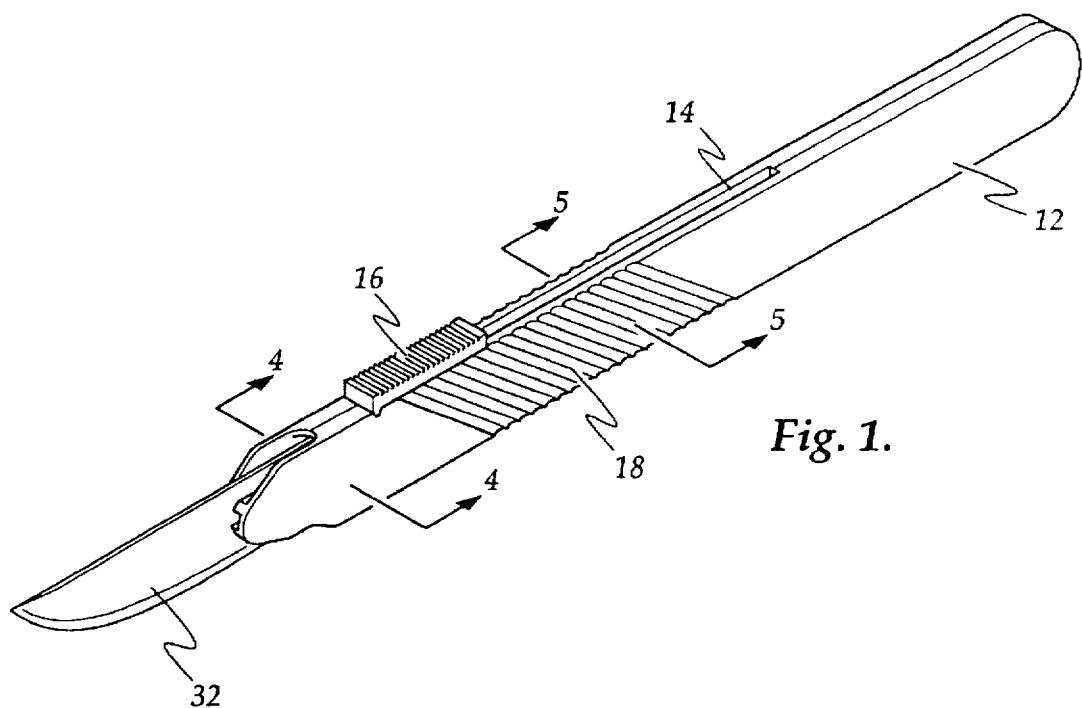
FIG. 1 is a perspective view of a scalpel according to the invention with the blade in the operative position.
Figure 2:
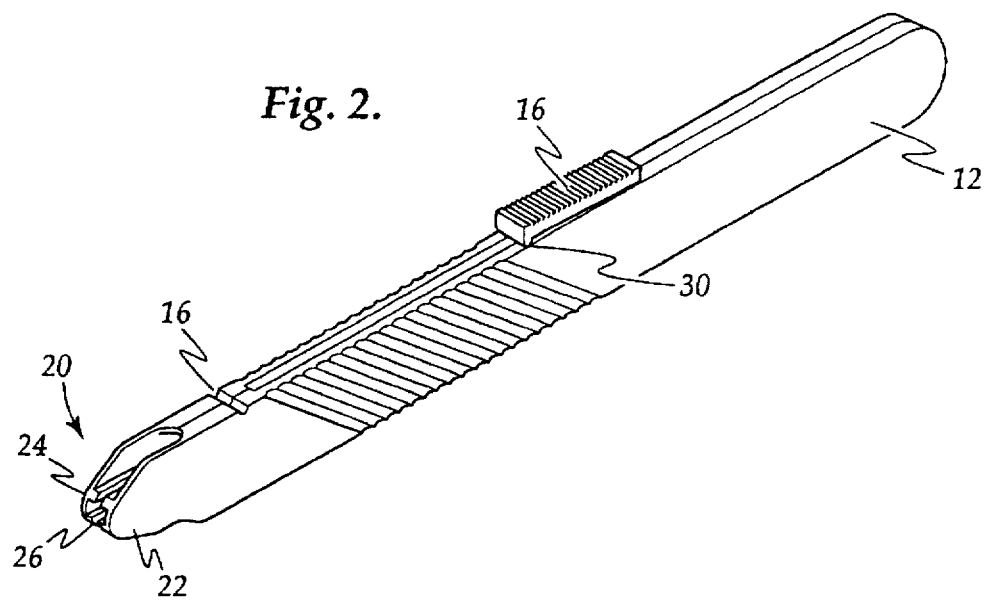
FIG. 2 is a perspective view of the scalpel of FIG. 1 with the blade in the inoperative position.

As can be seen in FIGS 1 and 2, a retractable blade scalpel has a hollow handle 12 open at one end 20 and having longitudinally extending slot 14 along its upper surface. Slot 14 receives the shank of an engagement means in the form of tab 16 which is a part of mandrel 34. The sides of handle 12 carry a series of corrugations 18 which enhance the grip of the user of the scalpel. The sides of handle 12 extend beyond the opening 20 and form a pair of jaws 22, 24. Stiffening ribs 26 are formed on jaws 22, 24 as can be more clearly seen in FIGS. 4 and 5. A recess 28 is formed in the upper surface of handle 12 and can retain a projection 30 formed on the leading edge of tab 16.

Figure 3:
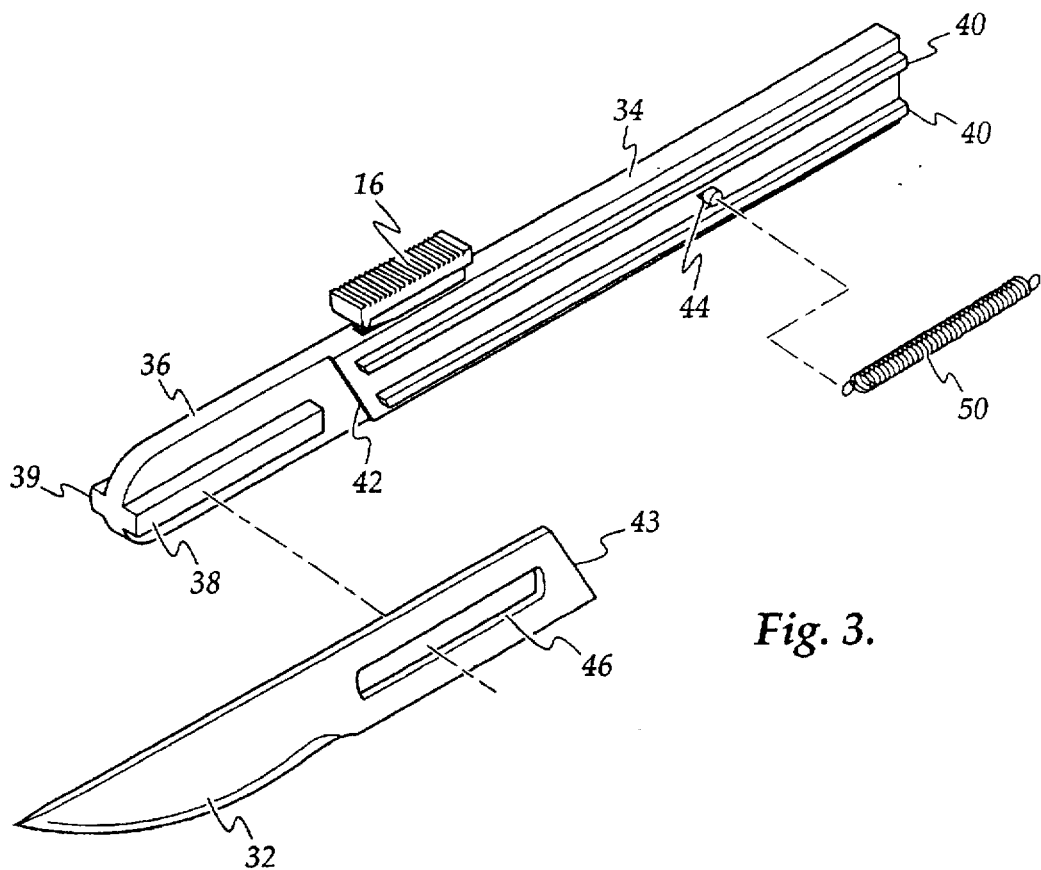
FIG. 3 is an exploded perspective view of a mandrel, (with resilient means removed) blade and biasing means.
Figure 4:
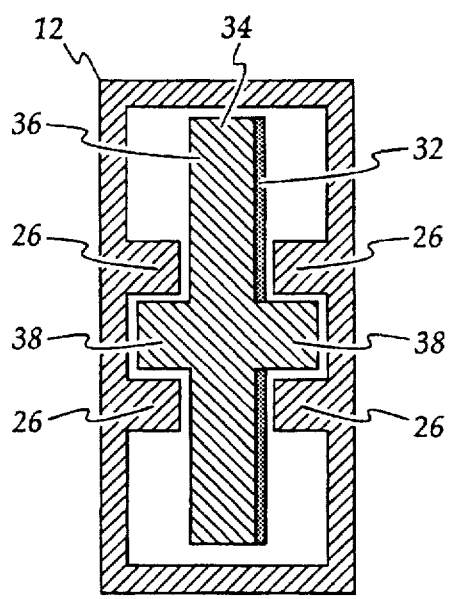
FIGS. 4 and 5 are cross sections along lines 4—4 and 5—5 of FIG. 1 respectively.

As is best seen in FIGS 3 and 4, mandrel 34 has a web 36 at one end of which a pair of ribs 38 constitute both stiffening means and mounting posts on which blade 32 is mounted by means of cutout 46. The distal end of blade 32 is angled at 48 to bear against angled support shoulder 42 on mandrel 34. At the distal end of mandrel 34 a pair of stiffening ribs 40 are located on either side of web 36. Post 44 is formed on web 36 and in use spring 50 is hooked over post 44 and the other end of spring 50 attached to post 52 which extends inwardly from the inner surface of handle 12 (see FIG. 5) to form biasing means for biasing the mandrel towards the position in which the blade is retracted.

Figure 5:
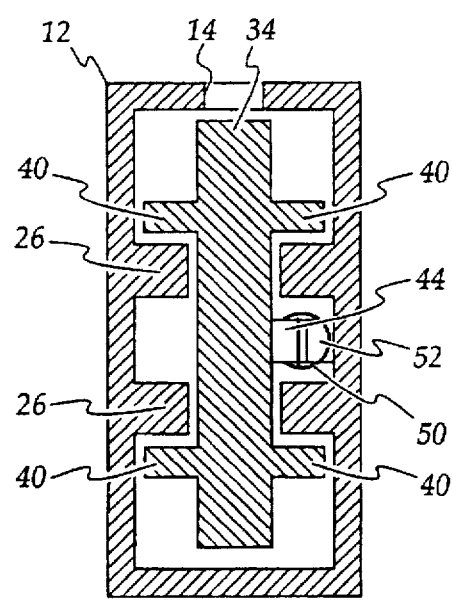

Handle 12 and mandrel 34 may be formed from a suitable durable plastics material. Handle 12 is stiffened by ribs 26 and mandrel 34 is stiffened by ribs 38 and 40. As can be seen in FIG. 4, in the operating position with the blade 32 extending through opening 20, ribs 38 closely cooperate with ribs 26 and the internal sidewalls of jaws 22 and 24 to guide and closely support the blade 32 within the handle thereby minimizing the potential for lateral and vertical play in blade 32 under operating conditions. Similarly as can be seen in FIG. 5, ribs 40 closely cooperate with ribs 26 and the internal sidewalls of handle 12 to guide the mandrel within the handle.

Figure 6:
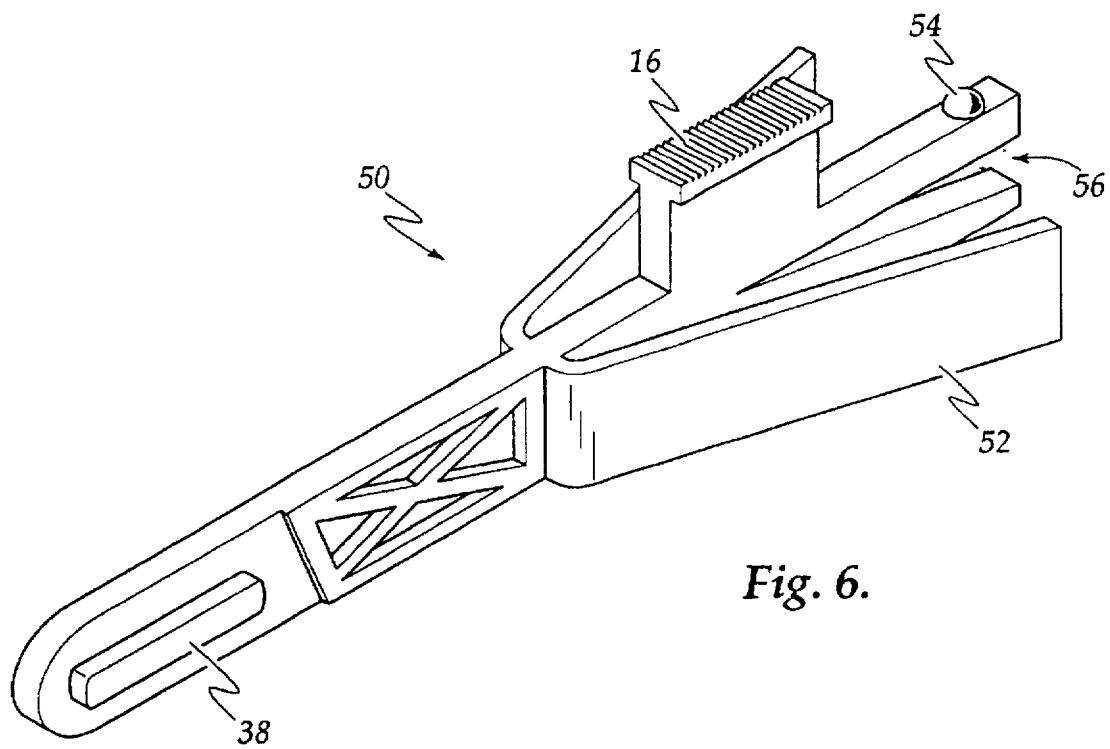
FIG. 6 is a perspective view of an alternative mandrel with resilient means.
Figure 9:
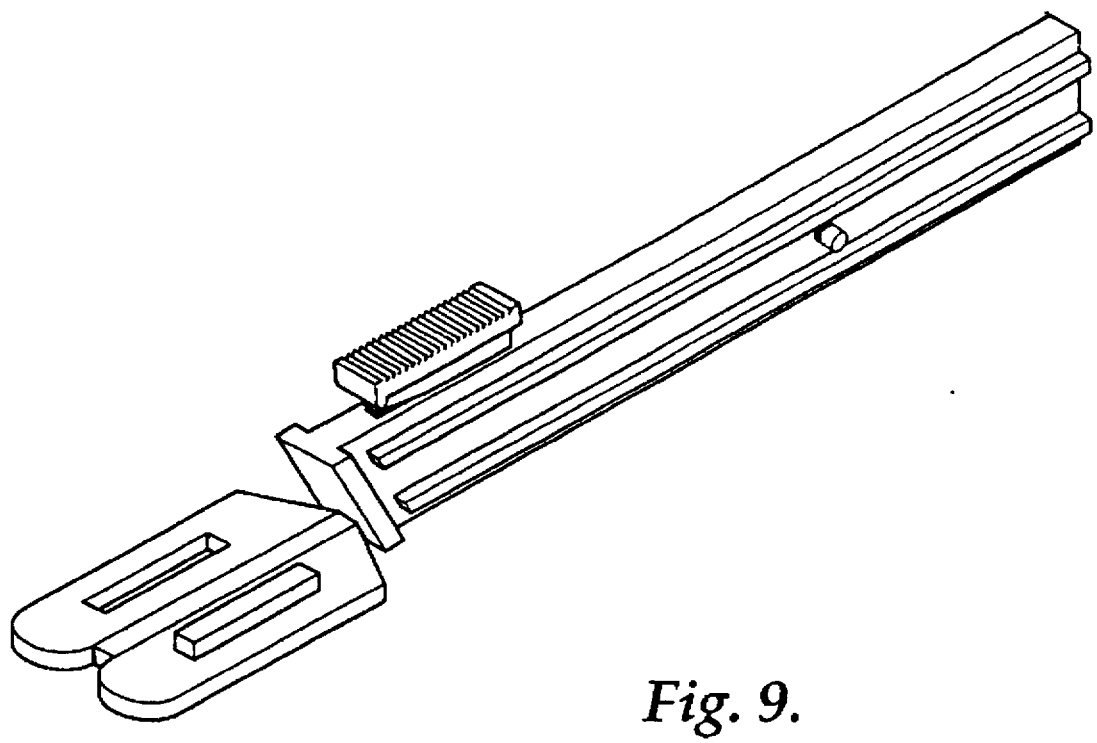
FIG. 9 is a perspective view of an alternative mandrel (with resilient means removed).

In an alternative arrangement illustrated in FIG. 9, the mandrel can include an alternative mounting arrangement to that described above. In this alternative, the mounting end of the mandrel is bifurcated to form arms pivotally mounted on an extension of the mandrel body. The arms respectively have a recess and a complementary projection. The projection is adapted to be closely received within the recess in a friction fit. The projection is dimensioned to be closely received within a cutout of the blade which is sandwiched between the bifurcated arms. Whilst FIG. 9 shows the arms pivoting downwardly from an extension of the lower mandrel body, the arms may be mounted to the mandrel body in other manners. For example, the arms may pivot upwardly from an extension of the upper mandrel body Referring to FIGS. 6 and 7, there is illustrated a mandrel including resilient means according to the invention. For simplicity the blade member is not shown.

Figure 7:
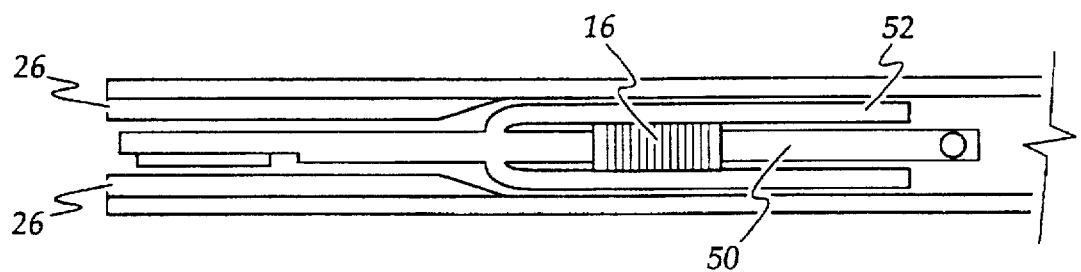
FIG. 7 is a plan view of the mandrel of FIG. 6 shown in sliding engagement in a complementary handle.

Mandrel 50 includes rib 38 which acts as a mounting post for the blade member and cooperates with rib 26 to guide the mandrel. Mandrel 50 may include a second rib on the side of the mandrel opposite to the side on which the blade member mounts to cooperate with the other rib 26. In contrast to the handle shown in FIGS. 1 to 5, ribs 26 do not extend the full length of the interior of the handle. Rather, they terminate with a profile which is complementary to the leading shoulder of the resilient wings 52 as shown in FIG. 7. It will be understood that this profile causes a camming effect which assists in limiting lateral play between the mandrel and handle when in the operative position.

Mandrel 50 includes engagement means in the form of tab 16.

Mandrel 50 also includes resilient means in the form of laterally and rearwardly extending wings 52 which, in use bear against the inner surface of the handle as shown in FIG. 7. The resilient means also assists in limiting lateral play between the mandrel and handle when in the operative position.

Mandrel 50 includes restraining means in the form of a projecting member 54 adapted to be received in receiving means disposed in the handle.

Mandrel 50 is resilient and bifurcated at 56 whereby manual force on engagement means 16 disengages the projecting member 54 from the receiving means.

Figure 8:
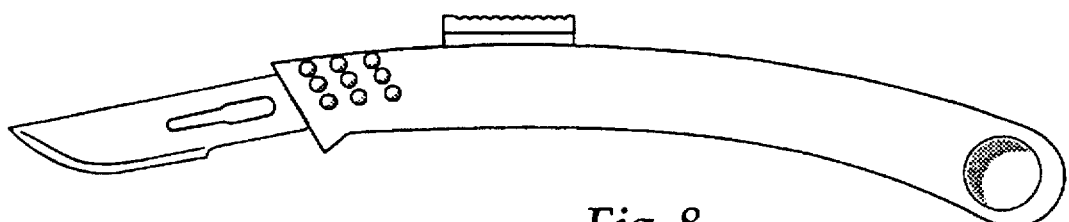
FIG. 8 is an elevational view of another scalpel according the invention.

Referring to FIG. 8, there is shown a scalpel in accordance with the invention. In this embodiment, the handle and mandrel are curved for ergonomic reasons.

Suitable materials for the mandrel and handle include light-weight metal and durable plastic material.

It will be appreciated that the retractable scalpel in accordance with this invention has a number of advantages. The stiffness provided by the stiffening ribs, the close tolerance of mandrel within the handle and the guiding interplay between the respective ribs each provide an element of stability against lateral and vertical movement of the blade under operating conditions. This can be important in certain surgical procedures where force is required. The single use non-reusable locking arrangement is particularly beneficial in guarding against cuts and needle stick-type injury to both medical personnel and in particular to waste disposal staff.

The scalpel in accordance with the invention has a good strength to weight ratio, is simple to manufacture and can be mass produced relatively inexpensively in comparison with known scalpels.

It will of course be realized that whilst the above has been given by way of an illustrative example of this invention, all such and other modifications and variations hereto, as would be apparent to persons skilled in the art, are deemed to fall within the broad scope and ambit of this invention as is hereinafter claimed.

We claim:

1. A scalpel including:

a handle;

a mandrel closely received within said handle, said mandrel being adapted to support a blade member and having engagement means for operative engagement by a user for movement of said mandrel within said handle;

biasing means for biasing said mandrel from an operative position to an inoperative position within said handle; and restraining means for restraining said mandrel in said operative position against the action of said biasing means, wherein said mandrel includes resilient means which bears against an inner surface of said handle when said mandrel is in said operative position.

2. A scalpel as claimed in claim 1, wherein said mandrel includes mounting means for mounting said blade member thereon, said mounting means constituting mandrel stiffening means and being adapted to guide said mandrel for movement within said handle.

3. A scalpel as claimed in claim 2, wherein said handle includes handle stiffening means cooperable with said mandrel stiffening means to guide said mandrel.

4. A scalpel as claimed in claim 1, and including locking means actuable upon retraction of said mandrel from said operative position to non-releasably lock said mandrel in said inoperative position.

5. A scalpel as claimed in claim 1, wherein said handle includes a longitudinally extending slot, said engagement means being adapted to extend through said slot.

6. A scalpel as claimed in claim 1, wherein said restraining means includes a projecting member on said engagement means and receiving means on said handle for releasably receiving said projecting member therein.

7. A scalpel as claimed in claim 6, wherein said projecting member is biased into engagement with said receiving means.

8. A scalpel as claimed in claim 1, wherein said resilient means are a pair of laterally and rearwardly extending wings.

* * * * *